US011537898B2

(12) United States Patent
Hegde et al.

(10) Patent No.: US 11,537,898 B2
(45) Date of Patent: Dec. 27, 2022

(54) GENERATIVE STRUCTURE-PROPERTY INVERSE COMPUTATIONAL CO-DESIGN OF MATERIALS

(71) Applicant: Samsung Electronics Co., Ltd., Suwon-si (KR)

(72) Inventors: Ganesh Hegde, Houston, TX (US); Harsono S. Simka, Saratoga, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 282 days.

(21) Appl. No.: 16/799,410

(22) Filed: Feb. 24, 2020

(65) Prior Publication Data

US 2021/0103822 A1  Apr. 8, 2021

Related U.S. Application Data

(60) Provisional application No. 62/909,648, filed on Oct. 2, 2019.

(51) Int. Cl.
*G06N 3/08* (2006.01)
*G06N 20/20* (2019.01)
(Continued)

(52) U.S. Cl.
CPC ............. *G06N 3/084* (2013.01); *G06F 30/13* (2020.01); *G06F 30/27* (2020.01); *G06N 3/0454* (2013.01); *G06N 20/10* (2019.01); *G06N 20/20* (2019.01)

(58) Field of Classification Search
CPC ...... G06N 3/084; G06N 3/0454; G06N 20/10; G06N 20/20; G06N 3/0472; G06N 3/088;
(Continued)

(56) References Cited

U.S. PATENT DOCUMENTS 6,763,309 B2  7/2004  Kieken et al.
7,292,958 B2  11/2007  Ceder et al.
(Continued)

FOREIGN PATENT DOCUMENTS

CN  108596994 A  9/2018
CN  111144565 A  5/2020
(Continued)

OTHER PUBLICATIONS

Blaschke, Thomas, et al., "Application of generative autoencoder in de novo molecular design," arxiv.org, Cornell University Library, Nov. 2017, XP080839053, 13 pages.
(Continued)

*Primary Examiner* — Brandon J Miller
(74) *Attorney, Agent, or Firm* — Lewis Roca Rothgerber Christie LLP (57) ABSTRACT

A method and a system for material design utilizing machine learning are provided, where the underlying joint distribution p(S,P) of structure (S)-property (P) relationships is explicitly learned simultaneously and is utilized to directly generate samples (S,P) in a single step utilizing generative techniques, without any additional processing steps. The subspace of structures that meet or exceed the target for property P is then identified utilizing conditional generation of the distribution (e.g., p(P)), or through randomly generating a large number of samples (S,P) and filtering (e.g., selecting) those that meet target property criteria.

20 Claims, 6 Drawing Sheets

(51) Int. Cl.
*G06N 20/10* (2019.01)
*G06F 30/13* (2020.01)
*G06F 30/27* (2020.01)
*G06N 3/04* (2006.01)

(58) Field of Classification Search
CPC ........ G06N 20/00; G06N 7/005; G06F 30/13; G06F 30/27; G16C 60/00; G16C 20/50; G16C 20/70
See application file for complete search history.

(56) References Cited

U.S. PATENT DOCUMENTS

| | | | |
|---|---|---|---|
| 7,882,052 | B2 | 2/2011 | Szathmary et al. |
| 8,671,369 | B2 | 3/2014 | Ahn |
| 10,043,261 | B2 | 8/2018 | Bhaskar et al. |
| 10,360,506 | B2 | 7/2019 | O'Brien et al. |
| 2017/0039469 | A1 | 2/2017 | Majumdar et al. |
| 2017/0161635 | A1 | 6/2017 | Oono et al. |
| 2018/0032663 | A1 | 2/2018 | Yoo et al. |
| 2018/0120479 | A1 | 5/2018 | Wood et al. |
| 2018/0225426 | A1 | 8/2018 | Murthy |
| 2019/0155977 | A1 | 5/2019 | Hegde et al. |
| 2019/0251459 | A1 | 8/2019 | Han et al. |
| 2019/0302290 | A1* | 10/2019 | Alwon .................. G01V 1/282 |
| 2019/0354801 | A1* | 11/2019 | Sohn .................. G06K 9/6219 |
| 2019/0354804 | A1* | 11/2019 | Ros Sanchez ....... G06K 9/6257 |
| 2020/0201905 | A1 | 6/2020 | Kaufman et al. |
| 2020/0363485 | A1 | 11/2020 | Sun et al. |
| 2020/0394275 | A1* | 12/2020 | Gecer Ulu ........... G06N 3/0454 |
| 2021/0304847 | A1* | 9/2021 | Senior .................. G06N 3/0445 |

FOREIGN PATENT DOCUMENTS

| | | |
|---|---|---|
| WO | 2017/094899 A1 | 6/2017 |
| WO | WO 2018/220368 A1 | 12/2018 |

OTHER PUBLICATIONS

Dong, Yuan, et al., "Inverse Structural Design of Graphene/Boron Nitride Hybrids by Regressional GAN," arxiv.org, Cornell University Library, Aug. 2019, XP081466951, 31 pages.

Nigam, AkshatKumar, et al., "Augmenting Genetic Algorithms with Deep Neural Networks for Exploring the Chemical Space," ICLR 2020, arxiv.org, 2020, XP081579685, 14 pages.

Schmidt, Jonathan, et al., "Recent advances and applications of machine learning in solid-state materials science," NPJ Computational Materials, Aug. 2019, XP055733799, 36 pages.

Yang, Zijiang, et al., "Microstructural Materials Design via Deep Adversarial Learning Methodology," arxiv.org, Cornell University Library, 2019, XP081015042, 34 pages.

EPO Extended Search Report dated Dec. 11, 2020, issued in corresponding European Patent Application No. 20179214.0 (12 pages).

Oleksii Prykhodko et al., "A De Novo Molecular Generation Method Using Latent Vector Based Generative Adversarial Network", Hit Discovery, Discovery Sciences, Biopharmaceutical R&D, AstraZeneca, & Department of Computer Science and Engineering, Gothenburg, Sweden, 27 pgs, Jun. 20, 2019.

Keith T. Butler et al., "Machine Learning For Molecular And Materials Science", https://doi.org/10.1038/s41586-018-0337-2, pp. 547-555, Jul. 25, 2018.

Xiaolin Li et al. "A Deep Adversarial Learning Methodology For Designing Microstructural Material Systems", Proceedings of the ASME 2018 International Design Engineering Technical Conferences & Computers and Information in Engineering Conference IDETC/CIE, Aug. 26-29, 2018, 14pgs., Quebec City, Canada.

Artur Kadurin, et al., druGAN: An Advanced Generative Adversarial Autoencoder Model for de Novo Generation of New Molecules with Desired Molecular Properties in Silico, Molecular Pharmaceutics, 2017, pp. 3098-3104, vol. 14, ACS Publishing, U.S.

Benjamin Sanchez-Lengeling, et al., Inverse molecular design using machine learning: Generative models for matter engineering, Science, 2018, pp. 360-365, vol. 361, The American Association for the Advancement of Science, U.S.

Benjamin Sanchez-Lengeling, et al., Optimizing distributions over molecular space. An Objective-Reinforced Generative Adversarial Network for Inverse-design Chemistry (ORGANIC), 2017, pp. 1-18, ChemRxiv, U.S. Website: https://chemrxiv.org/articles/ORGANIC_1_pdf/5309668/3.

Geun Ho Gu, et al., Machine learning for renewable energy materials, Journal of Materials Chemistry A, Aug. 7, 2019, pp. 17096-17117, vol. 7, No. 29, The Royal Society of Chemistry, U.K.

Lin-Wang Wang, A special purpose computer for ab initio molecular dynamics simulations, Aug. 18, 2008, 30 Pages, Lawrence Berkeley National Laboratory, U.S. Website: https://escholarship.org/uc/item/2874t8zr.

Rafael Gómez-Bombarelli, et al., Automatic Chemical Design Using a Data-Driven Continuous Representation of Molecules, 2017, pp. 1-26, U.S.

Zhaocheng Liu, et al., A Generative Model for Inverse Design of Metamaterials, 2018, pp. 1-15, Cornell University, U.S. Website: https://arxiv.org/abs/1805.10181.

U.S. Notice of Allowance dated Jun. 20, 2022, issued in U.S. Appl. No. 16/798,245 (9 pages).

U.S. Notice of Allowance dated Sep. 1, 2022, issued in U.S. Appl. No. 16/798,245 (5 pages).

* cited by examiner

GENERATIVE STRUCTURE-PROPERTY INVERSE COMPUTATIONAL CO-DESIGN OF MATERIALS

CROSS-REFERENCE TO RELATED APPLICATION

The present application claims priority to and the benefit of U.S. Provisional Application No. 62/909,648, entitled "GENERATIVE STRUCTURE-PROPERTY INVERSE COMPUTATIONAL CO-DESIGN OF MATERIALS", filed on Oct. 2, 2019, the entire content of which is incorporated herein by reference.

The present application is related to U.S. patent application Ser. No. 16/798,245, entitled "ELECTRONIC AND ATOMIC STRUCTURE COMPUTATION UTILIZING MACHINE LEARNING", filed on Feb. 21, 2020, which claims priority to and the benefit of U.S. Provisional Application No. 62/902,324, entitled "SEMICONDUCTOR DEVICE AND METHOD OF MAKING THE SAME", filed on Sep. 18, 2019, the entire contents of both of which are incorporated herein by reference.

FIELD

The present disclosure relates generally to systems and methods for material design utilizing machine learning.

BACKGROUND

Machine learning has been utilized for material discovery to meet the demand for materials with novel and/or improved properties.

Figure 1:
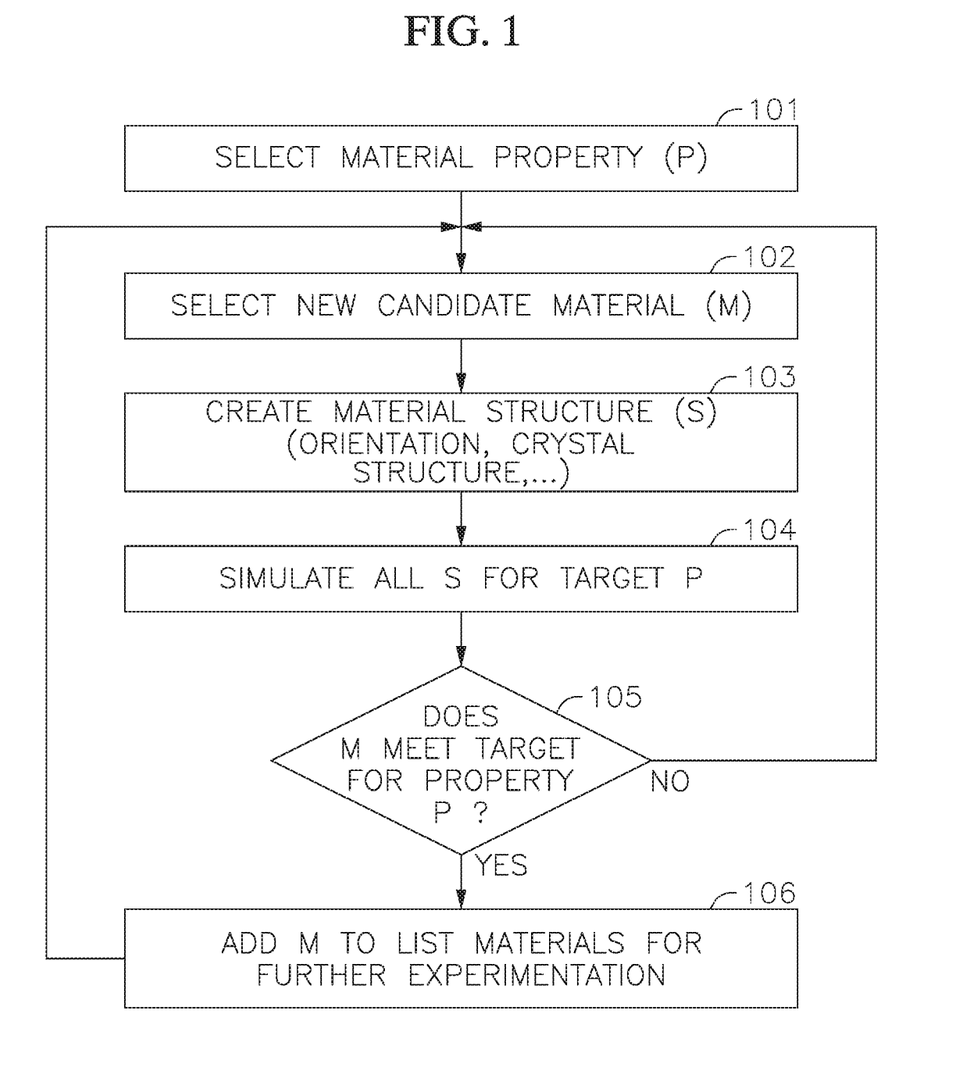
FIG. 1 is an illustration of a forward design process.

Referring to FIG. 1, a process for material discovery and design is shown. A physical property of interest (P) may be first identified in act 101. This could be, for instance, adhesion of a given material to a target material, resistivity, thermal conductivity, melting point, electromigration resistance, oxidation resistance, breakdown voltage, or a combination of relevant physical properties of interest for a given application.

A list of candidate materials (M) may then be gathered in act 102 based on prior knowledge and/or chemical intuition based on similarity with known materials having relevant values of property P. For each material M in the candidate list, various suitable potential material structures (S) may be chosen in act 103 (such as the crystal structure, orientation, etc.), and the property P may be calculated in act 104 for each of the potential structures at different length and time scales, such as (1) utilizing continuum level simulations (where the property P is calculated at human-relevant time scales and large (micron or greater) length scales) or (2) utilizing atom istic simulations (where the property P is calculated at the level of atoms and femtosecond time scales).

A decision is made in act 105. If the material M meets the target physical property, it may be considered as a favorable candidate for further experimentation and validation in act 106. The process may not stop here because there may be more than one favorable candidates for a property P with a variety of tradeoffs. If the material M does not meet the target for property P, the search continues until all the materials in the candidate set have been simulated.

For the purpose of this description, the process illustrated in FIG. 1 may be referred to as the "forward" mode of material design and discovery (e.g., "forward design"). The list of candidate materials may be selected based on prior knowledge of materials suitable for property P or on the basis of chemical intuition based on the similarity of a target material to other materials known to have a suitable value of P. While known physics/algorithm that maps structure S to property P is used in forward design, such a selection process may be blind to a number of target materials that may still be suitable for a particular application but lie either (1) outside the intuition of experts in a field, or (2) are dissimilar to known materials having a given property.

Additionally, forward design may be limited by the time required to simulate property P for structure S. Out of the possible universe of materials, only a tiny fraction can be simulated due to time constraints.

As such, there remains a need to improve the process of material discovery utilizing machine learning.

The above information in the Background section is only for the enhancement of the reader's understanding of the inventive concepts described herein and therefore it should not be construed as admission of existence or relevancy of the prior art.

SUMMARY

An aspect according to one or more embodiments of the present disclosure is directed toward a machine learning system for material design, where the underlying joint distribution p(S,P) of structure (S)-property (P) relationships is learned and is utilized to directly generate samples (S,P) in a single step (act) utilizing generative techniques, without any additional processing steps (acts).

An aspect according to one or more embodiments of the present disclosure is directed toward a method for material design utilizing machine learning, where the underlying joint distribution p(S,P) of structure (S)-property (P) relationships is learned and is utilized to directly generate samples having (S,P) in a single step utilizing generative techniques, without additional processing steps.

According to embodiments of the present disclosure, the subspace of structures (e.g., from a "whole" space representing all possible structures) that meets or exceeds the targets for property P are identified either utilizing conditional generation of the distribution (e.g., p(P)), or through randomly generating a large number of samples (S,P) and filtering (e.g., selecting) those that meet the target property criteria.

According to one or more embodiments of the present disclosure, a machine learning system to generate a structure (S) for a target property (P) includes a generative adversarial network (GAN), wherein the GAN includes: a latent space vector generator configured to generate random vectors, a generator network configured to receive the random vectors as input and to generate a tuple including both a simulated structure and a simulated property, and a discriminator network configured to be trained from a database including real structures and real properties, to distinguish the simulated structure and the simulated property from the real structure and the real property, and to send a loss function to the generator network, wherein the latent space vector generator, the generator network, and the discriminator network are arranged to learn an underlying joint probability distribution of structure-property p(S, P) simultaneously.

In one embodiment, the target property (P) includes one or more physical quantities, and the structure (S) includes a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation including species and/or coordinate tuples in succession.

In one embodiment, the system includes a single generator network.

In one embodiment, the generator network includes a first generator network to generate the simulated structure and a second generator network to generate the simulated property, and both the first generator network and the second generator network are configured to receive the random vectors from the same latent space vector generator.

In one embodiment, the generator network includes a first generator network to generate the simulated structure and a plurality of second generator networks, each to generate one of a plurality of simulated properties and both the first generator network and the plurality of second generator networks are configured to receive the random vectors from the same latent space vector generator.

In one embodiment, the discriminator network is configured to output a floating point or discrete count value.

In one embodiment, the system includes a computing device including graphics processing units (GPUs) and/or field programmable gate arrays (FPGAs).

According to one or more embodiments of the present disclosure, a method to generate a structure (S) for a target property (P) utilizing machine learning includes: training a discriminator network with a database including real structures and real target property, generating a simulated structure and a simulated property through a generator network, training the generator network so that the discriminator network fails to distinguish a difference between the simulated structure and the real structure from the database and learning an underlying joint probability distribution of structure-property p(S, P) simultaneously, and generating the structure for the target property utilizing the underlying joint probability distribution.

In one embodiment, the generating of the structure for the target property includes utilizing latent space partitioning p(P) to generate the structure (S) for the target property (P).

In one embodiment, the generating of the structure for the target property includes randomly generating a large number of samples (S,P) and filtering those that meet the target property (P).

In one embodiment, the target property (P) includes a physical quantity, and the structure (S) includes a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation containing (species, coordinates) tuples in succession.

In one embodiment, the method further includes generating random vectors through a latent space vector generator, wherein the generating of the simulated structure and the generating of the simulated property through the generator network utilizes the random vectors as inputs, and wherein the training of the generator network includes sending a loss function from the discriminator network to the generator network.

In one embodiment, the generator network includes a first generator network to generate the simulated structure and a second generator network to generate the simulated property, and both the first generator network and the second generator network are configured to receive the random vectors from the same latent space vector generator.

According to one or more embodiments of the present disclosure, a machine learning system to generate a structure (S) for a target property (P) includes a variational autoencoder (VAE), wherein the VAE includes an encoder network, a latent space, and a decoder network, wherein the encoder network is configured to receive a database including real structures and real properties as an input and compress the input to generate encoded vectors, mean and standard deviation of a distribution of the encoded vectors in the latent space, the decoder network is configured to be trained from the database including real structures and real properties, to decompress the encoded vectors to create simulated structure and simulated property, and to distinguish a difference between the simulated structure and the simulated property and the real structure and the real property, and to send a loss function to the encoder network, wherein the encoder network, the latent space, and the decoder network are arranged to learn an underlying joint probability distribution of structure-property p(S, P) simultaneously.

In one embodiment, the target property (P) includes one or more physical quantities, and the structure (S) includes a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation including species and/or coordinate tuples in succession.

In one embodiment, the system includes a computing device including graphics processing units (GPUs) and/or field programmable gate arrays (FPGAs).

According to one or more embodiments of the present disclosure, a method to generate a structure (S) for a target property (P) utilizing machine learning includes: inputting a database including real structures and real properties to an encoder network as an input and compressing the input to generate encoded vectors, mean and standard deviation of a distribution of the encoded vectors in a latent space, training a decoder network with the database including real structures and real properties, decompressing the encoded vectors to create simulated structure and simulated property by the decoder network, sending a loss function to the encoder network, and learning an underlying joint probability distribution of structure-property p(S, P) simultaneously.

In one embodiment, the method further includes generating the structure for the target property utilizing latent space partitioning p(P) to generate the structure (S) for the target property (P).

In one embodiment, the method further includes generating the structure for the target property through randomly generating a large number of samples (S,P) and filtering those that meet the target property (P).

In one embodiment, the target property (P) includes a physical quantity, and the structure (S) includes a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation containing (species, coordinates) tuples in succession.

This summary is provided to introduce a selection of features and concepts of embodiments of the present disclosure that are further described below in the detailed description. This summary is not intended to identify key or essential features of the claimed subject matter, nor is it intended to be utilized in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

Hereinafter, example embodiments will be described in more detail with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof.

The use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

The electronic or electric devices and/or any other relevant devices or components according to embodiments of the present invention described herein may be implemented utilizing any suitable hardware, firmware (e.g. an application-specific integrated circuit), software, or a combination of software, firmware, and hardware. The various components of these devices may be a process or thread, running on one or more processors, in one or more computing devices, executing computer program instructions and interacting with other system components for performing the various functionalities described herein. The computer program instructions are stored in a memory which may be implemented in a computing device utilizing a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present invention.

In the description below, the term "structure" may refer to atomic structure, arrangement of atoms in regular or irregular patterns in materials, and/or the spatial composition of atomic species in a material (e.g., a compound).

In the description below, the term "property" may refer to a physical property (such as boiling point, melting point, specific heat capacity, density, resistivity, thermal conductivity, electronic transmission, electromigration resistance, density of electronic levels, density of phononic levels, the mean free path of electron-phonon scattering, etc.); and/or an electronic structure property computed based on the atomic arrangement defined in the structure.

In the description below, the term "simultaneously" is used interchangeably with concurrently, synchronous and/or coincidental in time in reference to steps or acts in the generative process.

Throughout the current disclosure, the term "joint probability distribution p(S, P)" as used herein refers to the probability distribution representing the structure and property relationships, where both the structure S and the target property P, as two separate events, would be found simultaneously. The expression "the joint distribution p(S,P) of structure (S)-property (P) relationship is learned simultaneously" refers to a system or method that learns the relationship p(S,P) directly, simultaneously or concurrently. That is, when "the joint distribution p(S,P) of structure (S)-property (P) relationship is learned simultaneously," the joint distribution p(S,P) is not obtained from the individual probability p(S), the individual probability p(P), the conditional probability p(S|P), the conditional probability p(P|S), or another machine learned distribution.

Also, the expression "sample (S, P)" refers to a sample with the structure S and property P.

According to embodiments of the present disclosure, a method and a system for material design utilizing machine learning are provided, where the underlying joint probability distribution p(S,P) of structure (S)-property (P) relationships is learned simultaneously (i.e., explicitly learned simultaneously) and is utilized to directly generate samples (S,P) in a single step (act) utilizing generative techniques, without any additional processing steps (acts). The subspace of structures that meet or exceed the target for property P is then identified utilizing conditional generation of the distribution (e.g., p(P)), or through randomly generating a large number of samples (S,P) and filtering (e.g., selecting) those that meet target property criteria.

In a related art example, an alternative approach to forward design may be materials inverse design. Here, instead of utilizing intuition and prior knowledge to find a set of candidate materials suitable for the application, the target property P may be mapped on to structure S by utilizing a number of inverse design approaches. For example, inverse design approaches may be utilized for crystal structure prediction as shown in the schematic illustration of FIG. 5.

Figure 5:
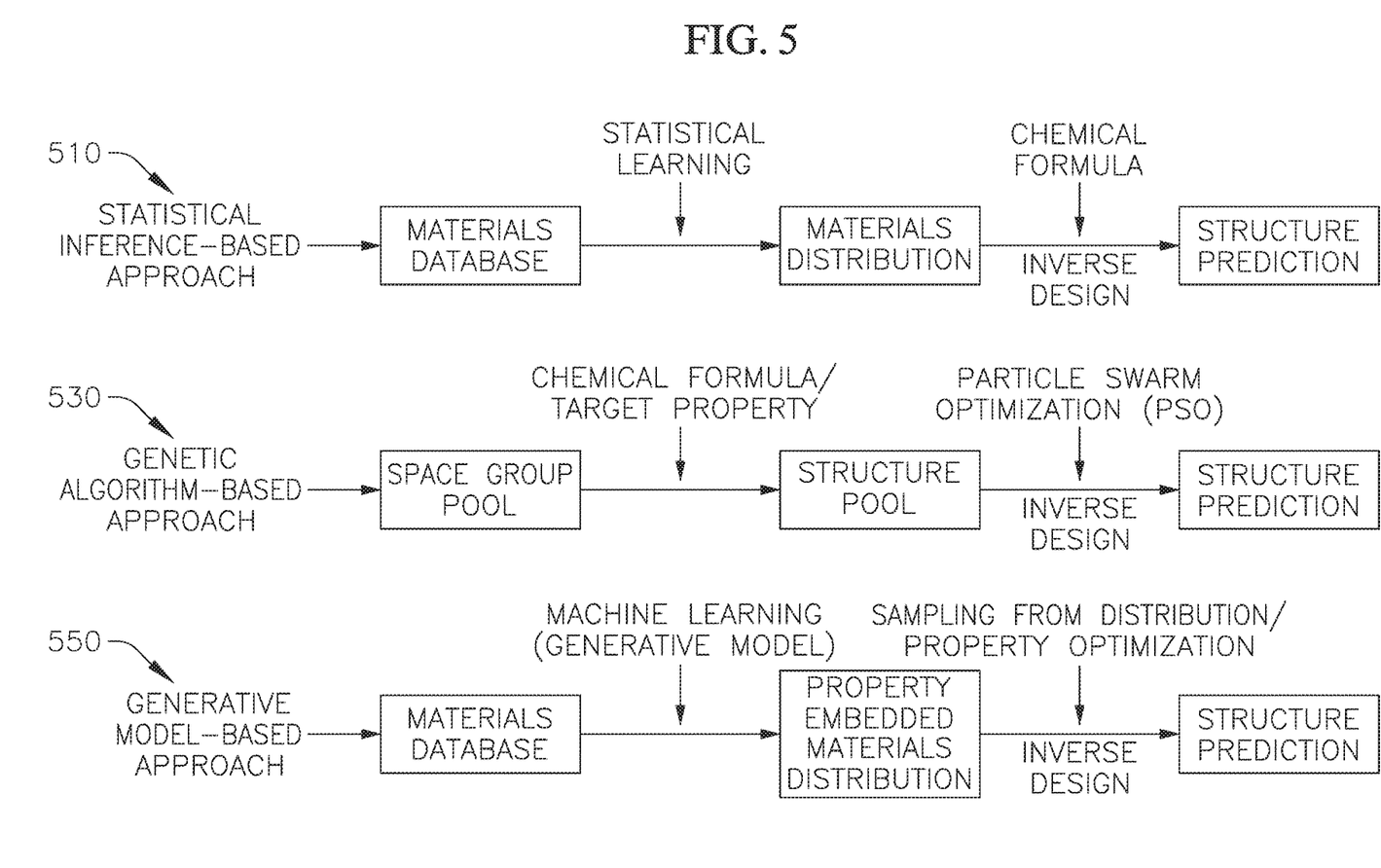
FIG. 5 is a schematic illustration of inverse design approaches for crystal structure prediction.

A statistical inference-based approach 510 entails learning structure-property relationships from a large database and utilizes this learning to predict the probability of a certain composition of materials to have a particular property, e.g., a particular crystal structure type. Here the output is the crystal (material) composition, while the input is the crystal structure. From a large group of binary and ternary materials, the composition versus ground state crystal structure mapping is extracted into a machine learning model. The model is then utilized to predict the crystal type for a composition having an unknown structure.

In a genetic algorithm-based approach 530, evolutionary and/or other global optimization techniques, such as particle swarm optimization (PSO), genetic algorithms, etc., are utilized to find a global optimum for an error function:

$$O(\sigma) = \sum_\alpha \omega_\alpha |P_\alpha(\sigma) - P_\alpha^{target}|$$

Here, the property $\alpha$ or the sum over a number of properties is computed in a space of candidate structures $\sigma$. A global minimum, i.e., the structure that optimizes the difference between desired properties and computed properties is obtained by utilizing heuristic optimization techniques.

Another approach may be a generative model-based approach 550. In a forward design problem, the probability distribution of interest is p(property|structure), the conditional probability of the structure at a given property. The category of problems where the distribution of the outputs is sought when the input is known are called discriminative problems. In an inverse approach, the conditionality is reversed—p(structure|property), is sought after. Such problems are generative problems. Generative approaches may include the use of generative adversarial networks (GAN) to identify geometric structures that match target optical spectra, as shown in FIG. 6.

Figure 6:
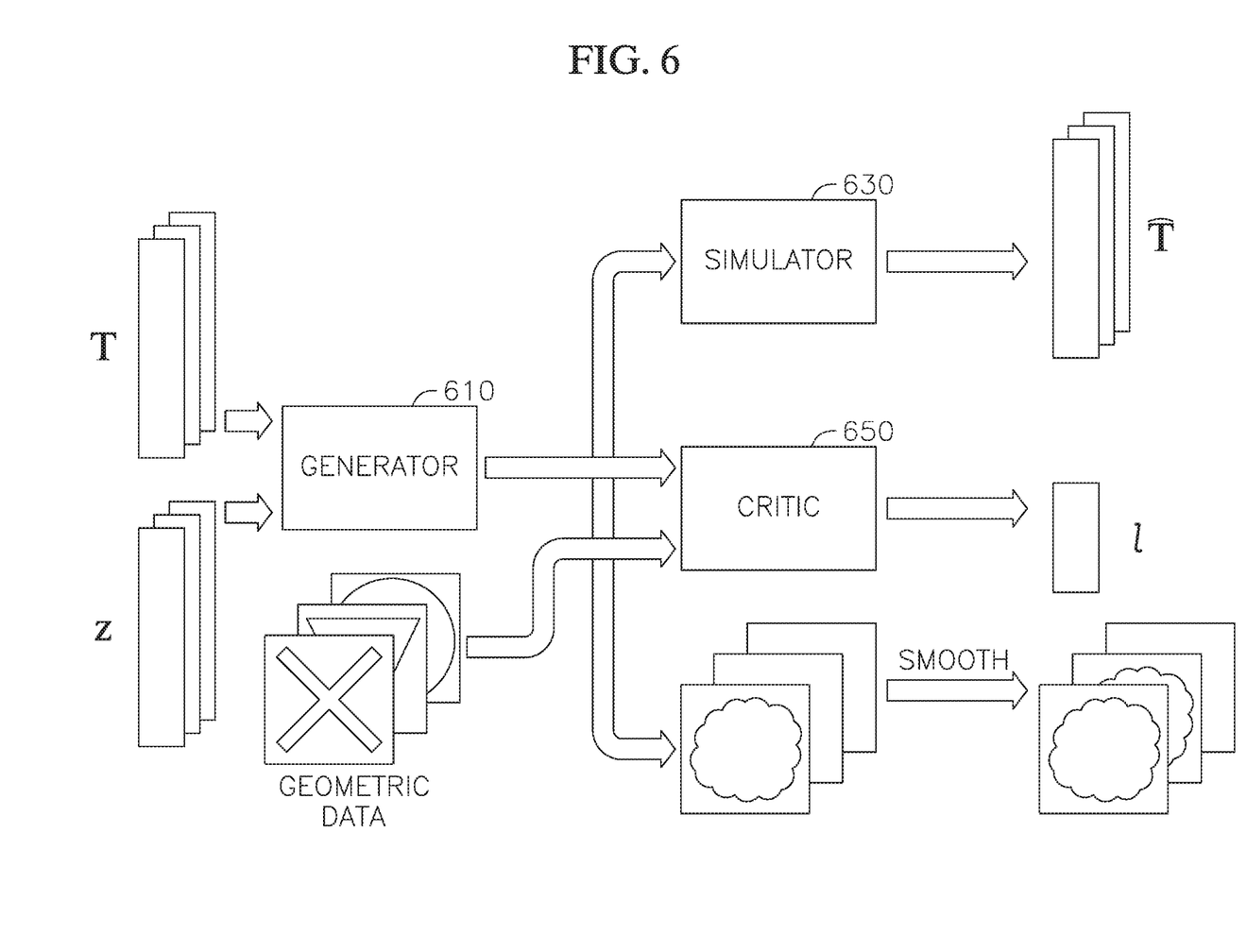
FIG. 6 is a schematic representation of inverse design approaches for a metasurface.

Referring to FIG. 6, metasurface design may be transitioned from trial-and-error approaches to neural network mediated inverse design by utilizing both simulation and inverse design to enact structure-property relationships to generate an optical spectrum from a metasurface and vice-versa. Both processes may be replaced by deep neural networks. The architecture of a network for artificial intelligence (AI)-based optical design may include three networks: the generator 610, the simulator 630, and the critic 650 as shown in FIG. 6. The generator may accept the spectra T and noise z and produce possible patterns. The simulator may be a pre-trained network that approximates the transmittance spectrum T^ for a given pattern at its output, and the critic may evaluate the distance of the distributions between the geometric data and the patterns from the generator. While training the generator, the produced patterns may vary according to the feedback obtained from the simulator and critic. Valid patterns may be documented during the training process, and may be smoothed to qualify as candidate structures, but additional steps (acts) will be required to identify the structure for a given property.

In the approaches shown in FIGS. 5-6, only one of the conditional probability distribution of the structure p(structure|property) or the probability distribution of the property p(property|structure) is obtained in a given process. None of these approaches utilize generative techniques to obtain the underlying joint distribution p(S, P) of structure (S)-property (P) relationship simultaneously and without any additional processing steps, e.g., in generating or predicting the new structures. In fact, in these methods, a number of steps are needed before a given structure (S) for a target property (P) is identified.

In contrast, the approach according to embodiments of the present disclosure may perform inverse design entirely in a generative framework without requiring any additional learning framework to bias the distribution towards desired/target properties. For example, reinforcement learning may not be needed (i.e., may not be included) in the present application (e.g., current method).

According to some example embodiments, the joint probability distribution of structures and properties of arbitrary materials can be obtained in a single step (act) instead of including intermediate steps (acts) and post processing. Additionally, according to some example embodiments, (S, P), i.e., structure and property, may be produced in a single step (act) without any intermediate or post processing steps (acts).

According to one or more embodiments of the present disclosure, a method for generating structure and property simultaneously includes learning the underlying statistical properties of the joint probability distribution of structure-property p(S, P) simultaneously, where no additional steps (acts) or computational processing are needed between the generation of the structure and the generation of the property. According to embodiments of the present disclosure, the joint distribution p(S,P) is not learned sequentially by learning the distribution of p(S), p(S|P), p(p) and/or p(P|S).

According to an embodiment of the present disclosure, the underlying joint probability distribution p(S,P) may be learned (or estimated) by a generative framework selected from, but not limited to, generative adversarial networks (GANs), any suitable variants thereof (such as deep convolutional GAN (DCGAN), Wasserstein GAN (WGAN), Fisher GAN (FGAN), etc.), variational autoencoders (VAE), any suitable variants thereof (such as Attention network), and/or combinations thereof (such as VAE-GAN).

Figure 2:
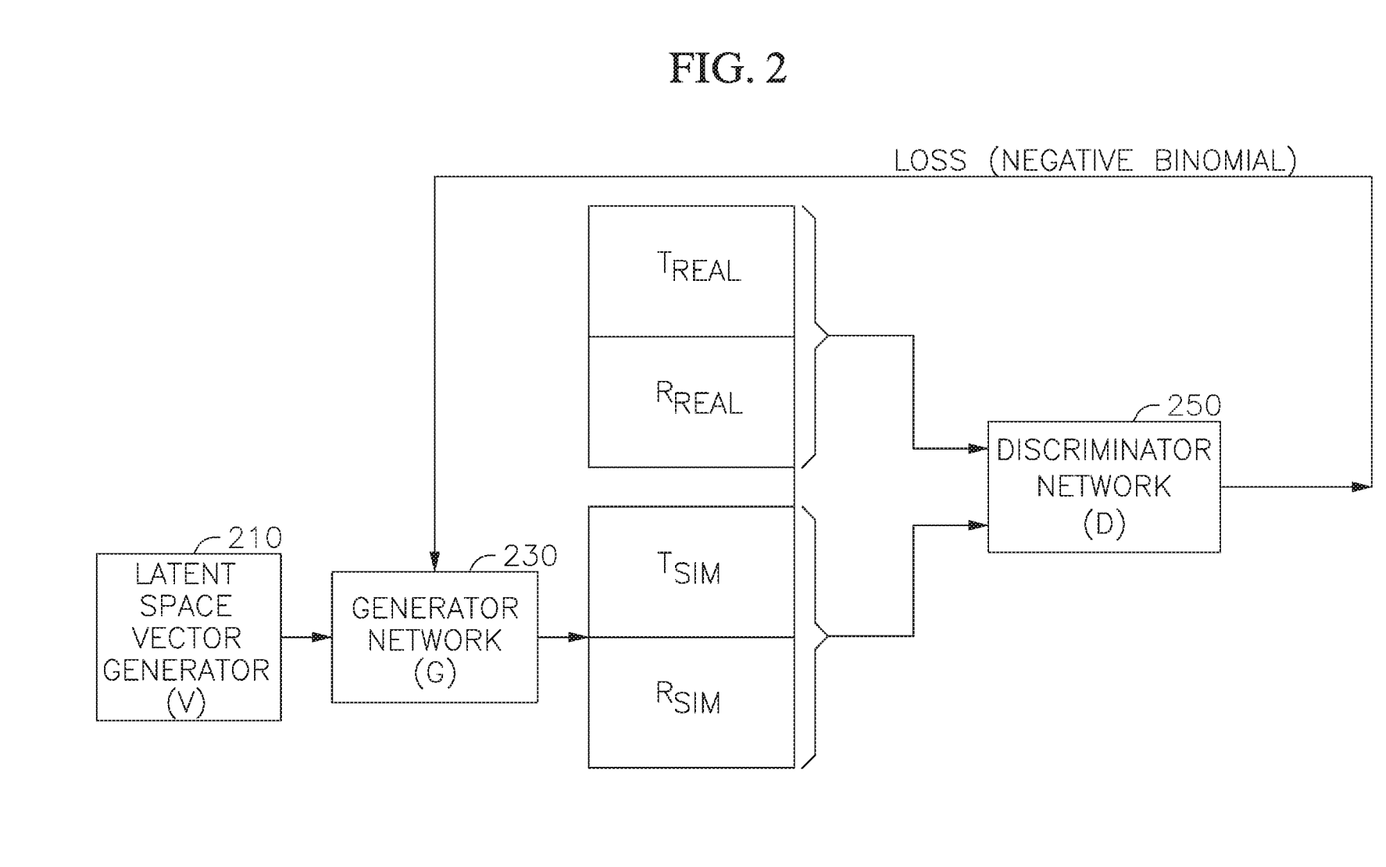
FIG. 2 is a schematic illustration of a system and a training process for a generative adversarial network (GAN) according to an embodiment of the present disclosure.

FIG. 2 is a schematic illustration of a system and a training process for a generative adversarial network (GAN) according to an embodiment of the present disclosure. The system includes a latent space vector generator (V) 210, a generator network (G) 230, and a discriminator network (D) 250.

In machine learning, an epoch is one iteration through all the training data. The training data is split into batches of various sizes. An initial pass in every training epoch teaches the discriminator what a "true" example looks like utilizing the real structure and real property pair. Subsequent passes in each training epoch are utilized to train the generator network (G) to produce simulated structure and simulated property that are indistinguishable from the real pair. By learning and training with the structure-property pair together (simultaneously), the system may learn the joint distribution of p(S,P) simultaneously.

In the training process (stage), the discriminator network (D) is trained utilizing both real structures ($R_{real}$) and real properties ($T_{real}$) simultaneously to learn a mapping function between the two. For example, actual materials with the target properties are utilized to train the discriminator network (D). By training the discriminator network (D) with both real structures ($R_{real}$) and real properties ($T_{real}$), the structure-property relation can be learned simultaneously (e.g., not sequentially after learning the structure before or after learning the structure separately).

In machine learning, latent space refers to an abstract multi-dimensional space containing feature values (i.e., vectors) that encodes a meaningful internal representation of externally observed events (such as the structure and the property of materials). Latent space aims to provide an understanding (or representation) of these events (structures and properties) to a computer through a quantitative spatial representation/modeling. Each attribute of the event is represented by one or more vectors in the latent space, and an event may be represented with a plurality of dimensions in the latent space.

In utilizing the generative adversarial network (GAN) according to an embodiment of the present disclosure, the latent space vector generator (V) generates purely random numbers of the desired dimensionality. For instance, the latent space vector generator (V) may output a purely random vector of any suitable dimensionality, e.g., a dimensionality of 10, such that all random numbers are drawn from a Gaussian distribution with zero mean and unit variance, i.e., the standard normal distribution. The idea behind utilizing a random number generator in this framework is that the meaning to these random vectors gets assigned "a posteriori", i.e., after the discriminator network (D) rejects samples for being fake (i.e., simulated). In the course of the training process, some form of order is being imposed on the vector space defined by the latent space vector generator such that a sub-space of the vectors being generated correspond to the desired sub-space (e.g., the sub-space that has the structure with the target property). In one embodiment of the present disclosure, the successful completion of the training procedure finds the subspace that corresponds to the distribution of structure-property pair with materials having the desired property.

The latent space vector generator (V) generates random vectors that are mapped to the property space and structure space, and the generator network (G) generates the simulated samples of ($T_{sim}$, $R_{sim}$) tuples including the simulated property $T_{sim}$ and the simulated structure $R_{sim}$ based on the random vectors provided from the latent space vector generator (V). Throughout the current description, "T" and "P" are utilized interchangeably to refer to the property, and "R" and "S" are utilized interchangeably to refer to the material structure.

These structure/property pairs are then fed into the trained discriminator network (D). If the discriminator network (D) can distinguish the difference between the real structure-property pair it was trained with and the simulated structure-property pair, i.e., if the generated samples ($T_{sim}$, $R_{sim}$) are recognized as fake, the difference is used to construct a loss function that is passed to the generator network (G), forcing the generator network (G) to modify its parameters to produce more realistic samples. The greater the difference is, the greater the loss function is. The training objective is to increase the error rate of the discriminative network (D) (i.e., to "fool" the discriminator network (D) so that it cannot distinguish the sample generated by the generator network (G) from the real structure-property pair).

The loss function may be any suitable type corresponding to the quantity being learned. For instance, if a continuous variable is being learned, the loss function may be a quantity such as root mean squared error. If a categorical (e.g., qualitative) variable is being learned, the loss may be cross-entropy, Kullback-Leibler divergence or similar measures. In one embodiment, a negative binomial loss function may be utilized for training the generator network (G) when the output data is discrete. However, embodiments of the present disclosure are not limited thereto, and other suitable loss functions may be utilized.

According to an embodiment of the present disclosure, the structure and/or property may include or consist of ordinal or count data. The discriminator network (D) may output a floating point (e.g., continuous floating point) or discrete count value instead of binary (True/False, 0/1) values. The loss function may be calculated based on the output of the discriminator network (D). For example, the loss function for count data may be defined utilizing Negative Binomial loss or Poisson loss.

At the end of the training process, in one embodiment, the discriminator network (D) may have, e.g., a 50% or greater probability of correctly classifying a generated sample as being fake (simulated) or not. The entire process is called adversarial generation of samples, because the generator network (G) and discriminator network (D) act as adversaries, each trying to outdo the other. The generator network (G) tries to create realistic samples, while the discriminator network (D) tries to spot fake samples and the two networks are locked in an adversarial process until training is complete, i.e., up until the generator network (G) generates fairly realistic samples of underlying (T, R) distribution.

When the GAN is trained to a point where its simulated structure-property pairs are statistically indistinguishable from the real structure-property pairs, the training is completed. At this stage, the join distribution of p(S,P) has been learned, and new materials that satisfy the target properties can be obtained by sampling the corresponding sub-space.

Figure 3:
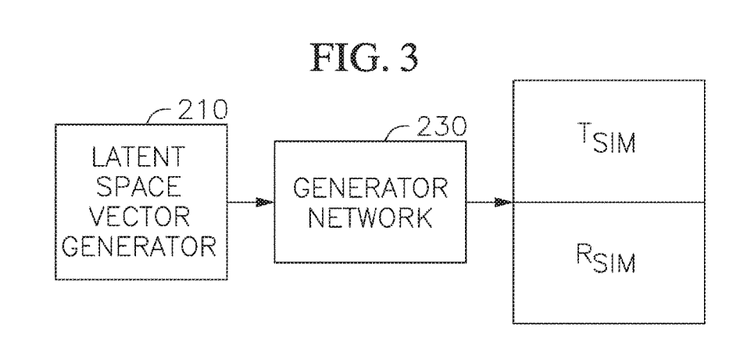
FIG. 3 is schematic illustration of a sample generation process according to an embodiment of the present disclosure.

Once the training process is complete, (T, R) samples that satisfy the target property P can be created by sampling the latent space through the generator network (G) as shown in FIG. 3. Referring to FIG. 3, the latent space vector generator (V) 210 produces random vectors for the generator network (G) 230, and the generator network (G) 210 transforms the random vectors to (S,P), i.e., a structure (S) that has the target property (P). The subspace of structures that meets or exceeds the targets for property P may be identified either through use of latent space partitioning (p(P)), or through simultaneous (or concurrently) generation of a large number of candidate structure/property pairs (S,P) followed by filtering to select candidates with the desired properties (P).

According to some example embodiments, the system and method may be applied to categorical, ordinal, integer and/or count properties in addition to continuous properties. For example, when the property P is the Ballistic Electronic Transmission of the material, the output representing the property according to an embodiment may be integer/count data. When the property is Density of states, the output representing the property may be continuous data. When the property is a class that the material belongs to, the output representing the property may be a categorical data.

According to an embodiment of the present disclosure, the target property may be any combination of two or more desirable physical quantities, such as resistivity, density of states, etc., while the structure may be an encoded vectorized representation in which elements of the structure vector represent atomic species in specific locations.

According to an embodiment of the present disclosure, the target property may be any combination of two or more desirable physical quantities, such as resistivity, density of states, etc., while the structure may be a floating point vectorized representation in which contiguous tuples of the structure vector represent variables (x, y, z) in Cartesian coordinates of a fixed atomic species. The system and method according to some example embodiments may be applicable to design any desirable materials, such as 1D, 2D, 3D, molecules, etc.

According to an embodiment of the present disclosure, the target property may be any combination of two or more desirable physical quantities, such as resistivity, density of states, etc., while the structure may be a mixed representation containing (species, coordinates) tuples in succession.

According to an embodiment of the present disclosure, the generative framework for structure and properties utilizes a single generative network (G) to generate both structure and property. Both structure and property can be vectors that are concatenated to each other, and then fed to the discriminator network (D).

According to another embodiment of the present disclosure, a single generative network is utilized for the structure generation while distinct generative networks are utilized for respective distinct properties from among a plurality of target properties. For example, a first generative network is utilized for the structure generation, a second generative network is utilized for a first property generation and a third generative network is utilized for a second property generation. The structure, the first property and the second property are then concatenated together.

Figure 4:
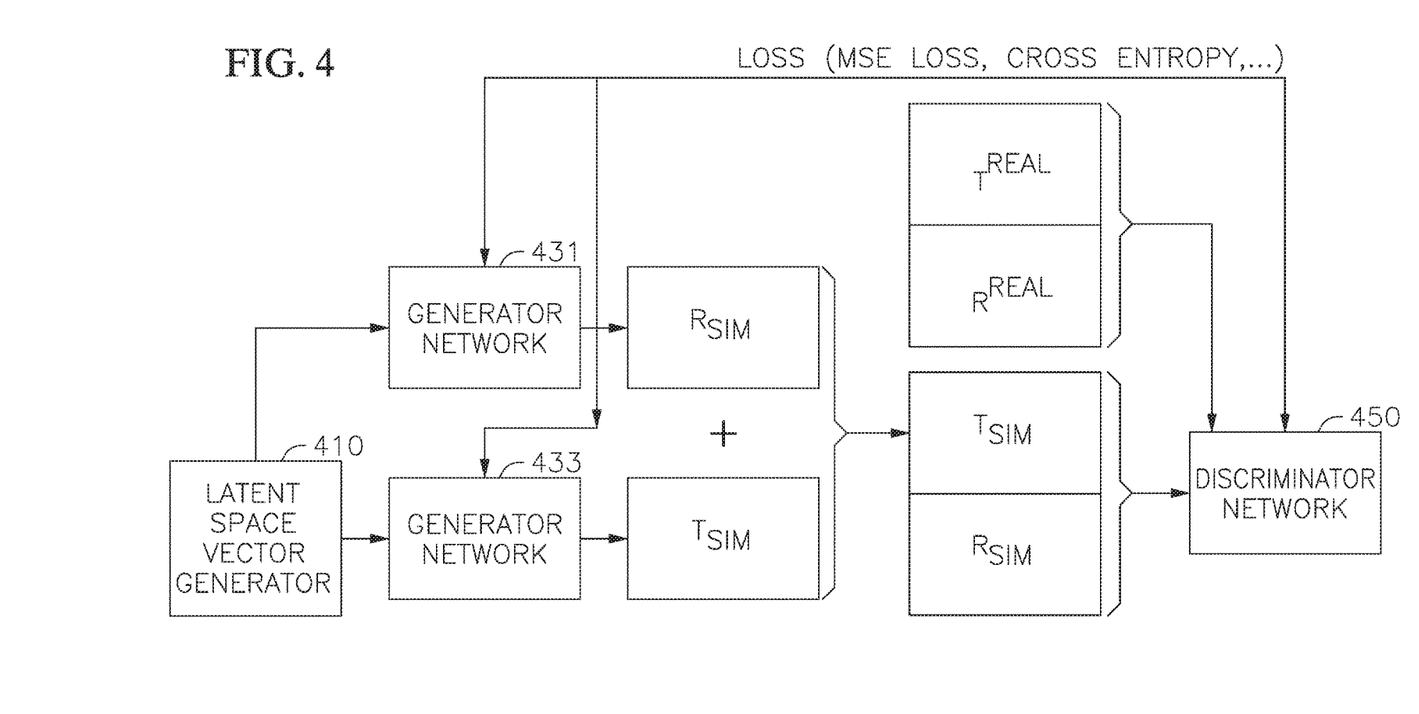
FIG. 4 is a schematic illustration of a system and a training process for a generative adversarial network (GAN) according to an embodiment of the present disclosure.

FIG. 4 is a schematic illustration of a system and a training process for a generative adversarial network (GAN) according to an embodiment of the present disclosure. Referring to FIG. 4, a latent space vector generator (V) 410 feeds into two generator networks (G) 431 and 433 that separately create structure (R) and property (T) vectors respectively, that are concatenated and fed to the discriminator network (D) 450. The loss from the discriminator network (D) is fed into both generator networks (G) during the training process.

The loss function may be Mean Squared Error (MSE), cross entropy, or any other suitable loss functions.

In MSE, the error is calculated by taking an average across the whole dataset of the squared difference between the distribution of the data generated by the GAN and the distribution of the real data.

In cross entropy loss function, the following Mathematical formulation may be utilized:

$$\text{CrossEntropyLoss} = -(y_i \log(\hat{y}_i) + (1-y_i)\log(1-\hat{y}_i))$$

In the cross entropy loss function, $y_i$ represents the actual value, and $\hat{y}$ represents the simulated value. When the actual label is 1 ($y_i=1$), the second half of the function disappears whereas in case where the actual label is 0 ($y_i=0$), the first half is dropped off. Cross-entropy for a binary or two-class prediction problem is calculated as the average cross-entropy across all examples.

While a generative adversarial network (GAN) is illustrated in FIGS. 2-4, the present disclosure is not limited thereto. According to an embodiment of the present disclosure, the underlying joint probability distribution p(S,P) may be learned utilizing the variational autoencoder (VAE). In one embodiment, a variational autoencoder (VAE) includes an encoder network, a latent space, a decoder network, and a loss function. The encoder network is a neural network that outputs a compressed representation z of data x. The decoder network is a neural network that learns to reconstruct the data x given the compressed representation z. Through training, the loss function gets reduced or minimized and the VAE learns a probability distribution of the data.

Figure 7:
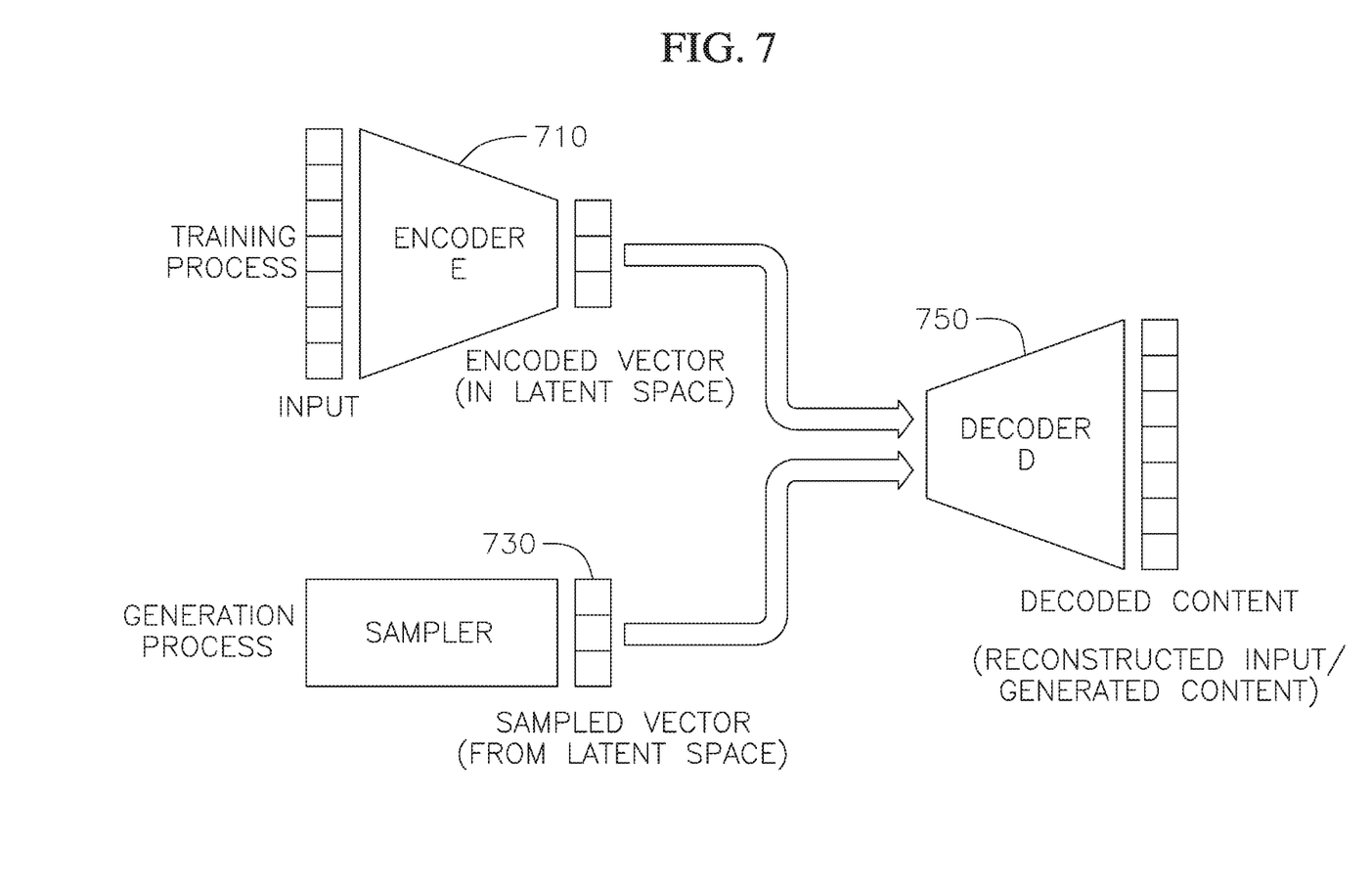
FIG. 7 is a schematic a system and a training process utilizing a VAE architecture according to an embodiment of the present disclosure.

In more detail, the encoder network is composed of Convolutional Layers, which compress the input and outputs a dense representation of the input, called encodings. This process where the encoder network compresses the data (from the initial space to the encoded space, also called latent space) is referred to as data compression or dimensionality reduction. In this process, the input is encoded as vectors with a probability distribution over the latent space. A point from the latent space is sampled from that distribution. The decoder network uses Deconvolutional Layers, which is the reverse of Convolutional Layers, and decompress the sampled point.

During the training process, the real structure and real property pair (i.e., the initial data) is fed to the encoder network. That is, both the real structure and the real properties are fed to the encoder network. The encoder network transforms the input as a vector distribution over the latent space, and learns the mean and standard deviation of the probability distribution. Then the decoder network takes the output of the encoder, and outputs a restructured version of the input. The difference between the restructured version of the input and the actual input is backpropagated as the loss function to adjust the weights of the neural networks of the encoder and decoder in an iterative optimization process so that at the end of the training process, the output of the decoder network is an acceptable approximation of or can't be distinguished from the initial data.

The loss function is composed of a "reconstruction term" (on the final layer), that tends to make the encoding-decoding scheme as performant as possible, and a "regularization term" (on the latent layer), that tends to regularize the organization of the latent space by making the distributions returned by the encoder close to a standard normal distribution. Through the training process, the loss function is minimized.

After the training is completed, i.e., the output of the decoder network can't be distinguished from the initial data, the VAE architecture can be utilized to obtain new structure-property pairs. Through the training process, the latent space becomes an encoded representation (of the structure-property pair), which when passed through a suitable decoder produces the desired output. To obtain a new structure for a target property, the learned joint distribution probability, mean and standard deviation are utilized to provide inputs from the latent space to be decoded by the decoder to generate (partake) new structure-property pairs that have the structures suitable to provide the target properties. A filter may be utilized to further select the material structures. In this process, the decoder would act similarly to the generator network of a Generative Adversarial Network and the encoder is not utilized.

FIG. 7 is a schematic illustration of a VAE architecture. Referring to FIG. 7, during the training process, an input is transformed by the encoder network 710 to a latent distribution (as an encoded vector) in the latent space 730. The encoded vector from the latent distribution is sampled by the decoder network 750 and transformed to a decoded output through the decoding process. During the generating process, a point from the latent space (as a sampled vector) 730 is selected and decoded by the decoder network 750 to produce a newly generated structure/property pair.

According to an embodiment of the present disclosure, the generative process may incorporate uncertainty estimation, which gives a measure of how confident the model is about its predictions. The uncertainty of predictions can be estimated utilizing any suitable techniques available, such as active learning, Bayesian learning, etc.

In one embodiment, the property of interest may be electronic transmission (T) while the structure (R) may be represented by categorical values representing atomic species at specific positions in a unit cell. Such a configuration is suitable for learning the joint structure-transmission distribution for alloys, such as a binary, ternary or quaternary alloys. Both T and R can be vectors that are concatenated to each other. In this embodiment, T and R are discrete. For example, T can take integer values while R can take categorical values.

According to some example embodiments, the method can be applied to the joint probability distribution of structure to multiple properties, e.g., structure←→(property 1, property 2,), relationships. For example, the first property may be the electronic transmission and the second property may be density of electronic levels. According to some example embodiments, the method can be made conditional on certain properties. For example, the method may be utilized to find p(S, P1|P2), i.e., the probability distribution of (S, P1) given P2, etc.

Further, the structure obtained from methods according to embodiments of the present disclosure are not specifically limited to molecular structures, and may further include atomic structure, arrangement of atoms in regular or irregular patterns in materials, and the spatial composition of atomic species in a material (e.g., compound) or a sample of a material.

The system may be implemented utilizing any suitable computing devices, such as those with graphics processing units (GPUs), field programmable gate arrays (FPGAs), or other suitable hardware.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims, and equivalents thereof.

What is claimed is:

1. A machine learning system to generate a structure (S) for a target property (P), the system comprising a generative adversarial network (GAN),
wherein the GAN comprises:
a latent space vector generator configured to generate random vectors,
a generator network configured to receive the random vectors as input and to generate a tuple comprising both a simulated structure and a simulated property, and
a discriminator network configured to be trained from a database comprising real structures and real properties, to distinguish the simulated structure and the simulated property from the real structure and the real property, and to send a loss function to the generator network,
wherein the latent space vector generator, the generator network, and the discriminator network are arranged to learn an underlying joint probability distribution of structure-property p(S, P) simultaneously.

2. The system of claim 1, wherein the target property (P) comprises one or more physical quantities, and the structure (S) comprises a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation comprising species and/or coordinate tuples in succession.

3. The system of claim 1, wherein the system comprises a single generator network.

4. The system of claim 1, wherein:
the generator network comprises a first generator network to generate the simulated structure and a second generator network to generate the simulated property, and
both the first generator network and the second generator network are configured to receive the random vectors from the same latent space vector generator.

5. The system of claim 1, wherein:
the generator network comprises a first generator network to generate the simulated structure and a plurality of second generator networks, each to generate one of a plurality of simulated properties and
both the first generator network and the plurality of second generator networks are configured to receive the random vectors from the same latent space vector generator.

6. The system of claim 1, wherein the discriminator network is configured to output a floating point or discrete count value.

7. The system of claim 1, wherein the system comprises a computing device comprising graphics processing units (GPUs) and/or field programmable gate arrays (FPGAs).

8. A method to generate a structure (S) for a target property (P) utilizing machine learning, the method comprising:
training a discriminator network with a database comprising real structures and real target property,
generating a simulated structure and a simulated property through a generator network,
training the generator network so that the discriminator network fails to distinguish a difference between the simulated structure and the real structure from the database and learning an underlying joint probability distribution of structure-property p(S, P) simultaneously, and generating the structure for the target property utilizing the underlying joint probability distribution.

9. The method of claim 8, wherein the generating of the structure for the target property comprises utilizing latent space partitioning p(P) to generate the structure (S) for the target property (P).

10. The method of claim 8, wherein the generating of the structure for the target property comprises randomly generating a large number of samples (S,P) and filtering those that meet the target property (P).

11. The method of claim 8, wherein the target property (P) comprises a physical quantity, and the structure (S) comprises a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation containing (species, coordinates) tuples in succession.

12. The method of claim 8, further comprising:
generating random vectors through a latent space vector generator, wherein the generating of the simulated structure and the generating of the simulated property through the generator network utilizes the random vectors as inputs, and
wherein the training of the generator network comprises sending a loss function from the discriminator network to the generator network.

13. The method of claim 12, wherein:
the generator network comprises a first generator network to generate the simulated structure and a second generator network to generate the simulated property, and
both the first generator network and the second generator network are configured to receive the random vectors from the same latent space vector generator.

14. A machine learning system to generate a structure (S) for a target property (P), the system comprising a variational autoencoder (VAE),
wherein the VAE comprises an encoder network, a latent space, and a decoder network,
wherein the encoder network is configured to receive a database comprising real structures and real properties as an input and compress the input to generate encoded vectors, mean and standard deviation of a distribution of the encoded vectors in the latent space,
the decoder network is configured to be trained from the database comprising real structures and real properties, to decompress the encoded vectors to create simulated structure and simulated property, and to distinguish a difference between the simulated structure and the simulated property and the real structure and the real property, and to send a loss function to the encoder network,
wherein the encoder network, the latent space, and the decoder network are arranged to learn an underlying joint probability distribution of structure-property p(S, P) simultaneously.

15. The system of claim 14, wherein the target property (P) comprises one or more physical quantities, and the structure (S) comprises a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation comprising species and/or coordinate tuples in succession.

16. The system of claim 14, wherein the system comprises a computing device comprising graphics processing units (GPUs) and/or field programmable gate arrays (FPGAs).

17. A method to generate a structure (S) for a target property (P) utilizing machine learning, the method comprising:
inputting a database comprising real structures and real properties to an encoder network as an input and compressing the input to generate encoded vectors, mean and standard deviation of a distribution of the encoded vectors in a latent space,
training a decoder network with the database comprising real structures and real properties,
decompressing the encoded vectors to create simulated structure and simulated property by the decoder network,
sending a loss function to the encoder network, and
learning an underlying joint probability distribution of structure-property p(S, P) simultaneously.

18. The method of claim 17, further comprising generating the structure for the target property utilizing latent space partitioning p(P) to generate the structure (S) for the target property (P).

19. The method of claim 17, further comprising generating the structure for the target property through randomly generating a large number of samples (S,P) and filtering those that meet the target property (P).

20. The method of claim 17, wherein the target property (P) comprises a physical quantity, and the structure (S) comprises a representation selected from an encoded vectorized representation in which elements of a structure vector represent atomic species in specific locations, a floating point vectorized representation in which contiguous tuples of a structure vector represent variables (x, y, z) of Cartesian coordinates of a fixed atomic species, and a mixed representation containing (species, coordinates) tuples in succession.

* * * * *